(12) United States Patent
Chouno (10) Patent No.: US 8,094,899 B2
(45) Date of Patent: Jan. 10, 2012

(54) MEDICAL IMAGE DIAGNOSTIC DEVICE (75) Inventor: Tomoaki Chouno, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 363 days.

(21) Appl. No.: 12/444,215

(22) PCT Filed: Oct. 3, 2007

(86) PCT No.: PCT/JP2007/069363
§ 371 (c)(1),
(2), (4) Date: Apr. 3, 2009

(87) PCT Pub. No.: WO2008/044572
PCT Pub. Date: Apr. 17, 2008

(65) Prior Publication Data
US 2010/0074475 A1    Mar. 25, 2010

(30) Foreign Application Priority Data

Oct. 4, 2006   (JP) .................................. 2006-272489

(51) Int. Cl.
*G06K 9/00* (2006.01)
(52) U.S. Cl. ..................................................... 382/128
(58) Field of Classification Search .......... 382/128–134; 128/920, 922
See application file for complete search history.

(56) References Cited

U.S. PATENT DOCUMENTS

| 2005/0053196 A1* | 3/2005 | Mostafavi ................ 378/98.12 |
| 2005/0054916 A1 | 3/2005 | Mostafavi et al. |
| 2005/0238216 A1 | 10/2005 | Yoden |

FOREIGN PATENT DOCUMENTS

| JP | 2004-313291 | 11/2004 |
| JP | 2005-160688 | 6/2005 |
| JP | 2005-218796 | 8/2005 |

* cited by examiner

*Primary Examiner* — David Mis
(74) *Attorney, Agent, or Firm* — Antonelli, Terry, Stout & Kraus, LLP.

(57) ABSTRACT

A medical diagnostic imaging apparatus is provided that is capable of accurately tracking motions of a moving organ that moves periodically over a plurality of periods. The medical diagnostic imaging apparatus includes a matching computation unit for performing a matching computation between a template extracted containing a tracking point on one image and another image, and a template extracting unit for extracting, from the other image, a region correlated with the template as a template of the other image by the matching computation, whereby a movement of the tracking point is tracked based on the extracted template. The template extracting unit extracts, as a key template, a region containing one or more tracking points set on an image at least one time phase within a motion cycle of the moving organ. The matching computation unit performs the matching computation using the key template in the vicinity of the time phase at which the key template is extracted.

20 Claims, 8 Drawing Sheets

MEDICAL IMAGE DIAGNOSTIC DEVICE

TECHNICAL FIELD

The present invention relates to a tracking technology for tracking movement of a moving organ in an image on a medical diagnostic imaging apparatus.

BACKGROUND ART

It is useful for diagnosis of cardiac lesion to quantitatively evaluate cardiac output of blood, heart chamber volume, and thickness of cardiac muscle. For this reason, evaluation of these cardiac functions is carried out by medical diagnostic imaging apparatus, such as ultrasonic diagnostic imaging apparatus, magnetic resonance diagnostic imaging apparatus, and X-ray CT diagnostic imaging apparatus.

For example, in diagnosis of cardiac functions using an ultrasonic diagnostic apparatus, movements of valves and cardiac muscle walls, wall thickness, changes of heart chamber volume are measured by setting a tracking point set on a wall of a cardiac muscle and finding out to what location the tracking point has moved in association with pulsation of the heart. This determination of displacement of the tracking point in association with heart pulsation is referred to as tracking of a tracking point, or tracking. There is a method of tracking a tracking point by extracting or setting a small region with an arbitrary shape that contains a tracking point and an adjacent region thereof on each of images and performing a correlation process for this small region between the images. This method is referred to as a template matching technique, and the small region with an arbitrary shape that contains the tracking point and an adjacent region thereof is referred to as a template.

A heart is non-rigid object that undergoes complicated motions and changes in shape complicatedly. Therefore, a tracking point is tracked by a conventional template matching technique, tracking operation error becomes very large. For this reason, the conventional template matching technique has been able to track only one cardiac cycle through three cardiac cycles.

In addition, tracking results of a tracking point by a template matching technique (position coordinates of the tracking point) contains errors originating from sampling, quantization, noise, image quality variations, and examiner's probe manipulation, and these errors accumulate in the course of processing a large number of frames. As a consequence, these errors are added to the tracking point, and a shift from the original position occurs, making it difficult to track the tracking point accurately.

In view of the error problem in each template matching computation, Patent Document 1 discloses a method for improving the accuracy of the tracking operation for a tracking point on a heart, which is a non-rigid object, by varying the size of the template in order to avoid the presence of mixed data of images having the different moving directions of the organ in the same template.

Patent Document 1: JP-A-2004-313291

DISCLOSURE OF THE INVENTION

Problems that the Invention is to Solve

Nevertheless, it is believed that the method disclosed in Patent Document 1 cannot eliminate the problem that the above-mentioned errors of template matching computation accumulate.

Specifically, the method disclosed in Patent Document 1 is such that errors in each individual template matching computation can be reduced by determining the size of the template taking complicated shape changes of the heart into consideration. However, even if the size of the template is varied over time, the process in which the next template is obtained by using the previous one of templates is repeated, so computation errors are accumulated inevitably. An error arises over time between the tracking point that is to be tracked originally and the tracking point obtained by the computation. As a consequence, there is believed to be a possibility that measurement accuracy degrades when the cardiac functions are measured based on the tracking point. Therefore, it is believed that further improvements in the template matching technique are necessary to measure the cardiac functions accurately.

It is an object of the invention to provide a medical diagnostic imaging apparatus that can accurately track motions of a moving organ that moves periodically over a plurality of periods.

Means for Solving the Problems

In order to solve the foregoing problems, a medical diagnostic imaging apparatus according to the invention comprises: an image data acquiring unit for acquiring a plurality of images of a moving organ of a test object that moves periodically; a display unit for displaying the images acquired by the image data acquiring unit; a matching computation unit for performing a matching computation between a template extracted containing a tracking point on one image with another image; a template extracting unit for extracting, from the other image, a region correlated with the template as a template of the other image by the matching computation; a storing unit for storing the template in association with a time phase at which it has been extracted; and a control unit for controlling each of the units, the medical diagnostic imaging apparatus being for tracking a movement of the tracking point based on the extracted template and being characterized in that:

the template extracting unit extracts, as a key template, a region containing one or more tracking points set on an image of the moving organ at least one time phase within a motion cycle; and the matching computation unit performs the matching computation using the key template in the vicinity of the time phase at which the key template is extracted.

In order to solve the foregoing problems, the invention provides a tracking point tracking method of tracking a desired tracking point over a plurality of images of a moving organ of a test object that moves periodically by a matching computation using a template, comprising the steps of:

(a) setting the tracking point on one image;
(b) extracting a region containing the tracking point as a template;
(c) extracting, by a matching computation between the template and another image, a region correlated with the template from the other image as a new template; and
(d) repeating the template extracting step (c) while changing the images, the method characterized in that:

in the step (a), one or more tracking points are set on an image of a desired time phase;

in the step (b), a region containing one or more tracking points set on the image of the desired time phase is extracted as a key template; and in the step (c), the matching computation is performed using the key template in the vicinity of the time phase of the image in which the key template is extracted.

Advantage of the Invention

The medical diagnostic imaging apparatus according to the invention can lessen accumulation of tracking errors by performing template matching using a key template in one or more time phases of a motion cycle over a lapse of time of motion of a moving organ, and therefore makes it possible to maintain accuracy of tracking over a multiplicity of motion cycles.

DESCRIPTION OF THE REFERENCE NUMERALS AND SIGNS

1: ultrasonic probe, 2: image data generating unit, 3: input unit, 4: control unit (CPU), 5: image data storing unit, 6: tracking point setting unit, 7: template storing unit, 8: template matching computation unit, 9: template extracting unit, 10: measurement computation unit, 11: measurement result recording unit, 12: display unit, 13: biological signal input unit, 14: R wave time phase image, 15: T wave time phase image, 121: tracking process stop mark, 122: probe holding direction correction guide, 141: input tracking point, 142: key template, 143: tracking point setting sequence number

BEST MODE FOR CARRYING OUT THE INVENTION

Figure 1:
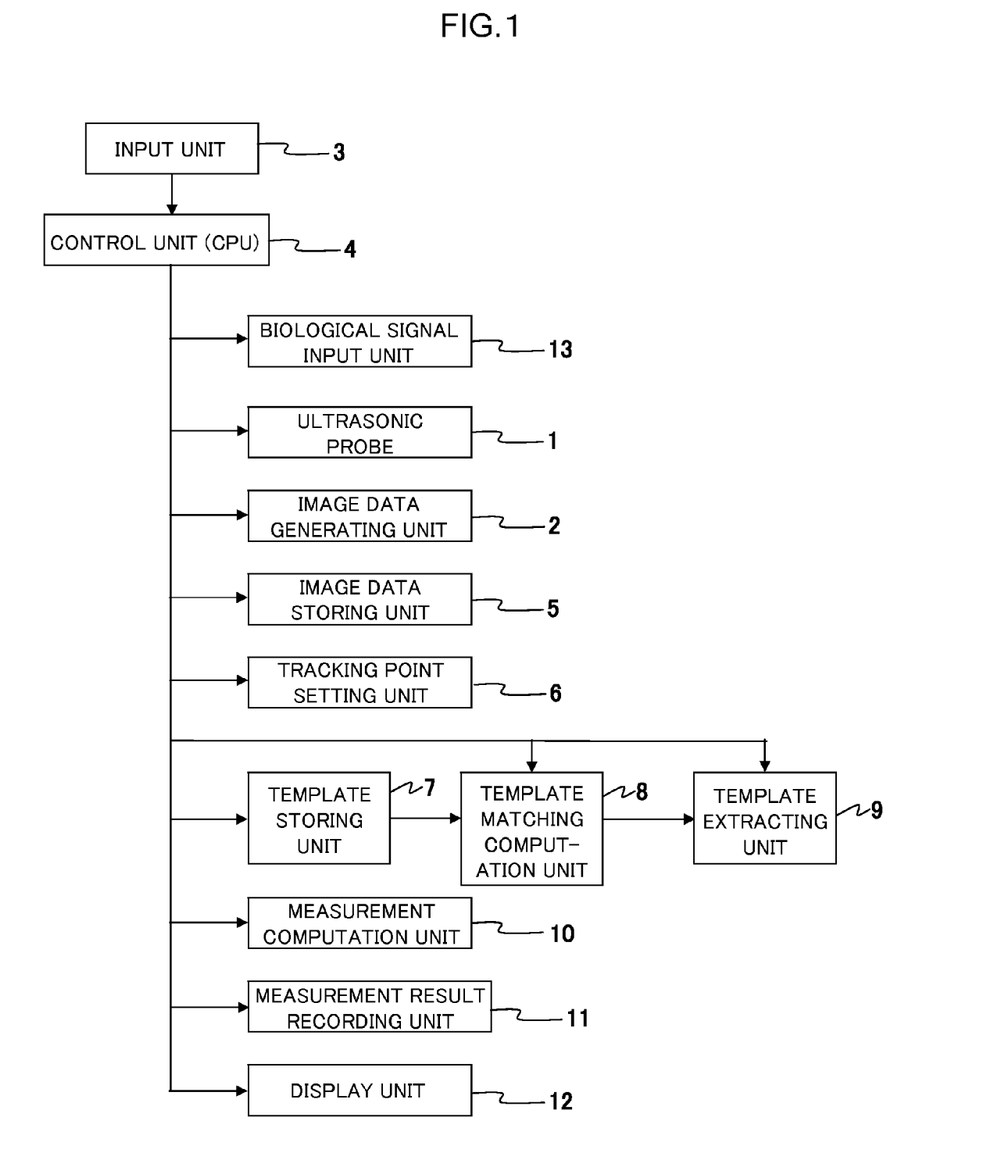
FIG. 1 is a block diagram of an ultrasonic diagnostic apparatus according to one example of the invention.

Hereinbelow, embodiments of a medical diagnostic imaging apparatus of the invention will be described with reference to the drawings. In the following, an example in which the invention is applied to a ultrasonic diagnostic imaging apparatus (hereinafter referred to as a ultrasonic diagnostic apparatus) is described as one example of the medical diagnostic imaging apparatus, but the invention may be applied likewise to other medical diagnostic imaging apparatus. FIG. 1 is a schematic block diagram of one example of a ultrasonic diagnostic apparatus having a tracking function to which the invention is applied and a cardiac function measuring function that uses the tracking function.

A ultrasonic diagnostic apparatus shown in FIG. 1 includes a ultrasonic probe 1 for performing transmission and reception of ultrasonic waves, a image data generating unit 2 for generating image data from ultrasonic wave reception signal received by the ultrasonic probe, an image data storing unit 5 for storing the image data, a control unit 4 (CPU) for controlling overall computation and timing thereof, an input unit 3 by which an examiner manipulates the apparatus, and a display unit 12. As shown in FIG. 1, the ultrasonic diagnostic apparatus also includes a tracking point setting unit 6 allowing an examiner to set the position of a tracking point to be tracked on a heart, in an image displayed on the display unit 12 in which the heart of a test object is visualized; a template storing unit 7 storing a key template in which a small image region containing the set tracking point and adjacent pixels thereof is extracted corresponding to the tracking point that has been set on the image, and a template that is extracted by a template matching computation; a template matching computation unit 8 performing a tracking operation for the set tracking point using the key template and the template that are read out from the template storing unit 7, a template extracting unit 9 extracting an optimum template by evaluating the computation results in the template matching computation unit 8, and deciding a tracking point from the template to thereby select and decide a tracking result; a measurement computation unit 10 computing physical parameters from the tracking result decided by the template extracting unit 9, which is a coordinate position of the tracking point; a measurement result recording unit 11 recording measurement results of the measurement computation unit 10; a display unit 12 displaying ultrasonic images based on the data from the image data generating unit 2 and the image data storing unit 5 and data recorded in the measurement result recording unit 11; and a biological signal input unit 13 taking in biological signals measured by an electrocardiograph and/or a heart rate meter attached to the test object.

The ultrasonic probe 1 transmits and receives ultrasonic waves to and from the test object. It has a shape such as a sector shape, a linear shape, and a convex shape, and has a known configuration.

The image data generating unit 2 converts the ultrasonic waves received by the ultrasonic probe 1 into electric signal, and thereafter generates B mode image data. The signal input from the ultrasonic probe 1 is converted into B mode image data through a preamplifier, a phased array adder, a logarithmic amplifier, an envelope detector, an A/D converter, and a scan converter, which constitute the image data generating unit 2.

The input unit 3 is a keyboard, a mouse, a trackball, or the like, which is disposed on the diagnostic apparatus. It is used by the examiner for adjusting image quality, setting input of tracking points, and inputting other information.

The control unit (CPU) 4 is for controlling the processes in various signal processing units, and has a ROM that stores software relating to later-described template matching computation and parameter computation in addition to ultrasonic wave transmission and reception and image generation.

The image data storing unit 5 is for storing acquired B mode moving image data and video format files that can be reproduced by a versatile PC (personal computer). It is a harddisk, a general-purpose memory, a frame memory, or the like.

The tracking point setting unit 6 is for setting while position (pixel) of the image displayed on the display unit 12 should be tracked among the coordinates of the tracking points input by the examiner from the input unit 3.

The examiner sets a position that he/she desires to track on the image displayed on the display unit 12 via the input unit 3 as a tracking point.

The template storing unit 7 extracts a set of pixels of a small image region containing the tracking point corresponding to the tracking point set by the input unit 3 and the tracking point setting unit 6, and stores the set of pixels as a template. The size of the template is, as one example, 40 pixels×40 pixels in pixel size, which is about 20 mm×20 mm in real space size, although it may depend on the number of tracking points set on the image. The shape may be any shape, such as a circular shape, an elliptical shape, a sector shape, and a rectangular shape, according to the resolution of the image. For simplicity, the shape is a square shape in the description herein. In the invention, in order to correct the tracking error of a tracking point during one cardiac cycle by switching a template, a template of at least one characteristic cardiac phase is required in one cardiac cycle. This template is referred to as a key template herein. Accordingly, the operator allows the display unit 12 to display a moving image of the heart on the display screen together with the electrocardiographic waveform, and also allows the display unit 12 to freeze an image of a characteristic cardiac phase of the electrocardiographic waveform, such as an R wave, or an R wave and a T wave, on the display screen. Then, the operator inputs a tracking point over an image of the R wave or the R wave and the T wave. Corresponding to the input tracking point that has been input over the image of the R wave or the image of the R wave and the T wave, a key template is extracted corresponding to each of the time phases, and the key template is stored in the template storing unit 7.

Figure 7:
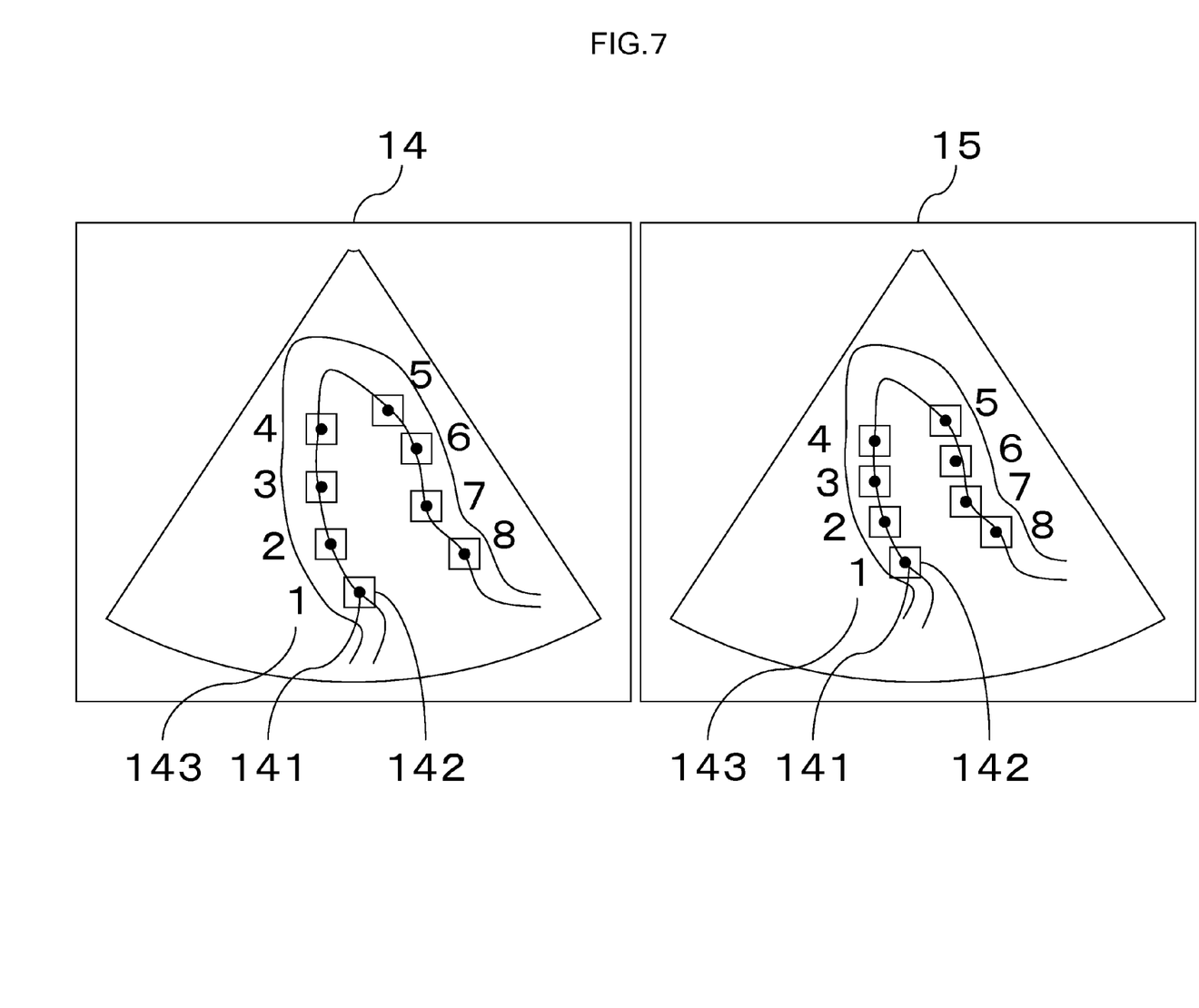
FIG. 7 is a view for illustrating the procedure of extracting respective key templates from an R wave time phase image and a T wave time phase image by taking correspondence therebetween.

When key templates are extracted respectively in a plurality of time phases, the same number of key templates is correlated and extracted on the images of the respective time phases. For example, when the key templates are extracted respectively for the R wave time phase and the T wave time phase, a tracking point (141) is input on an R wave time phase image (14) or on an R wave time phase image (14) and a T wave time phase image (15), as shown in FIG. 7. An adjacent region (142) containing the tracking point is the key template. In order to take correspondence in the sequence of tracking point setting positions between the R wave time phase and the T wave time phase, the tracking points are set commonly for both the R wave time phase and the T wave time phase, in a clockwise order or in an anti-clockwise order. Alternatively, setting sequence numbers (143) are stored and displayed while the tracking points are being set in the R wave time phase, and the setting sequence numbers (143) are displayed at the tracking point positions that have been set in the image of the R wave time phase at the same time as the T wave time phase image is displayed. Then, the examiner is advised to set tracking points on the image of the T wave time phase in the sequence according to the displayed numbers.

It should be noted that the characteristic time phase of motions of the heart may be, for example, an end-diastolic cardiac phase of the heart, an end-systolic cardiac phase, or both, in addition to the R wave and the T wave. In this case, the operator performs a B mode-M mode simultaneous measurement and simultaneous display of moving images of the heart during one cardiac cycle, freezes an end-diastolic image and an end-systolic image of the heart while reproducing the slow motion thereof, and inputs tracking points on the frozen images. Thereby, a template is extracted corresponding to the cardiac phases. The extracted templates are stored in the template storing unit 7 as the key templates.

Upon the start of the tracking point tracking operation process, the template matching computation unit 8 calculates the locations of the tracking points in the next frame by template matching computation using a set of pixels of the previously set tracking points and the adjacent pixels thereof as a template. The method for calculating the locations of the tracking points in the template matching computation unit 8 may be a tracking method such as using an interframe difference or an optical flow (Non-patent Document 1), or Kalman filter (Non-patent Document 2).

Non-patent Document 1: "Handbook for Electronics, Information and. Communication Engineers", the Institute of Electronics, Information and Communication Engineers, 1988, p. 1130 Non-patent Document 2: "Handbook for Electronics, Information and. Communication Engineers", the Institute of Electronics, Information and Communication Engineers, 1988, pp. 315-316 The template extracting unit 9 extracts one or a plurality of templates for a region containing the tracking points and the adjacent region in a certain frame (image) that have been subjected to a tracking operation using one or a plurality of templates by the template matching computation unit 8. Specifically, it evaluates whether or not the correlation value between the template of the previous frame and the next frame is equal to or greater than a predetermined threshold value, and if equal to or greater than the predetermined threshold value, it extracts the template with a greater correlation value as the template of the next frame to obtain the movement destination positions of the tracking points contained in the template.

The template extracting unit 9 determines that the tracking has failed if all the computed correlation values are equal to or less than the predetermined threshold value, and it instructs the template matching computation unit 8 to stop the tracking operation temporarily. At the same time, the display unit 12 displays an instruction for urging the examiner to correct the holding direction of the ultrasonic probe. In addition, in order to assist the correction, it superimposes the established tracking points that cover the period of one cardiac cycle during a normal period before the temporary stop of the tracking operation in sequence, on the actual ultrasonic image that is displayed, according to the time phase of the actual ultrasonic image.

The measurement computation unit 10 computes physical parameters such as tissue displacement and speed, or cardiac muscle wall thickness, area, heart chamber volume, and the like, in ultrasonic images of the heart based on the results tracked by the template matching computation unit 8 and the template extracting unit 9.

The measurement result recording unit 11 records the measurement results of the measurement computation unit 10 and at the same time outputs the measurement results to the display unit 12 so as to display the measurement values and a graphical representation image thereof.

FIRST EMBODIMENT

Figure 2:
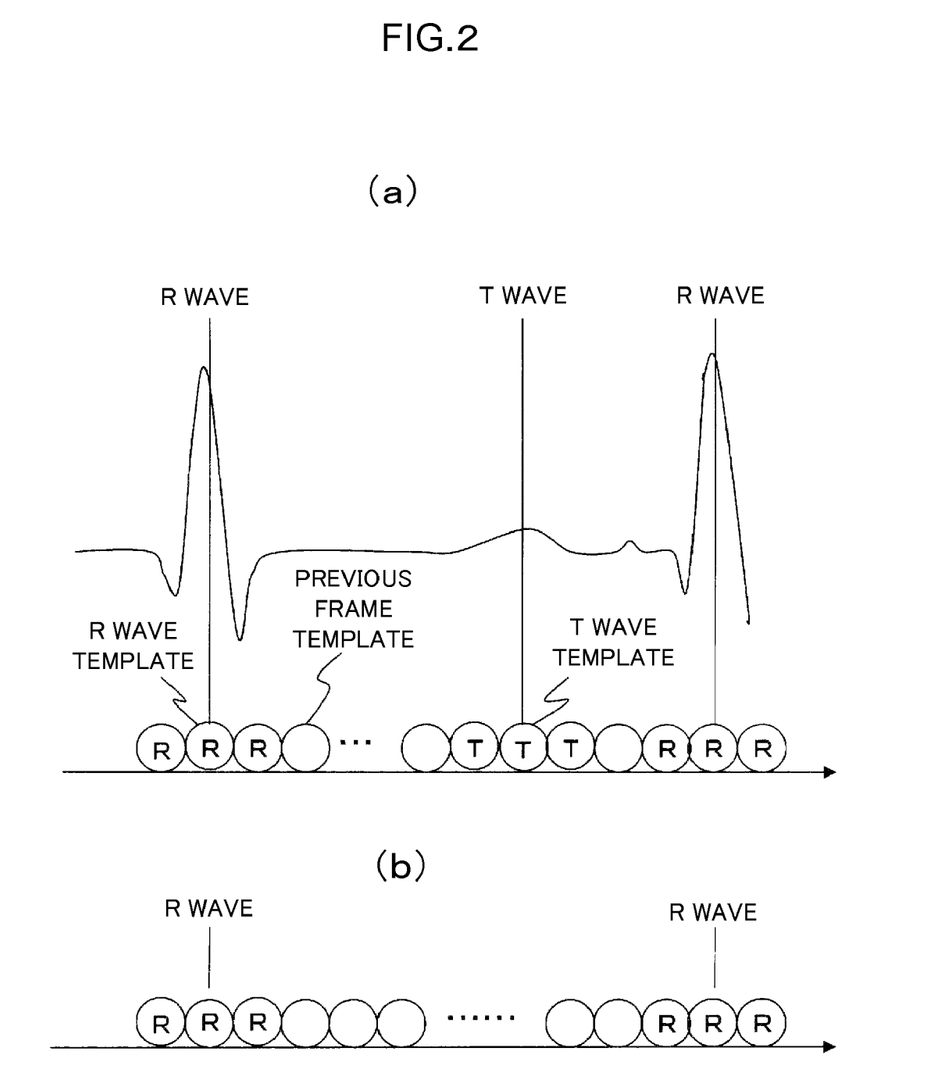
FIG. 2 is a view for illustrating the concept of the tracking operation in accordance with the template matching technique according to a first embodiment of the invention shown in FIG. 1.
Figure 3:
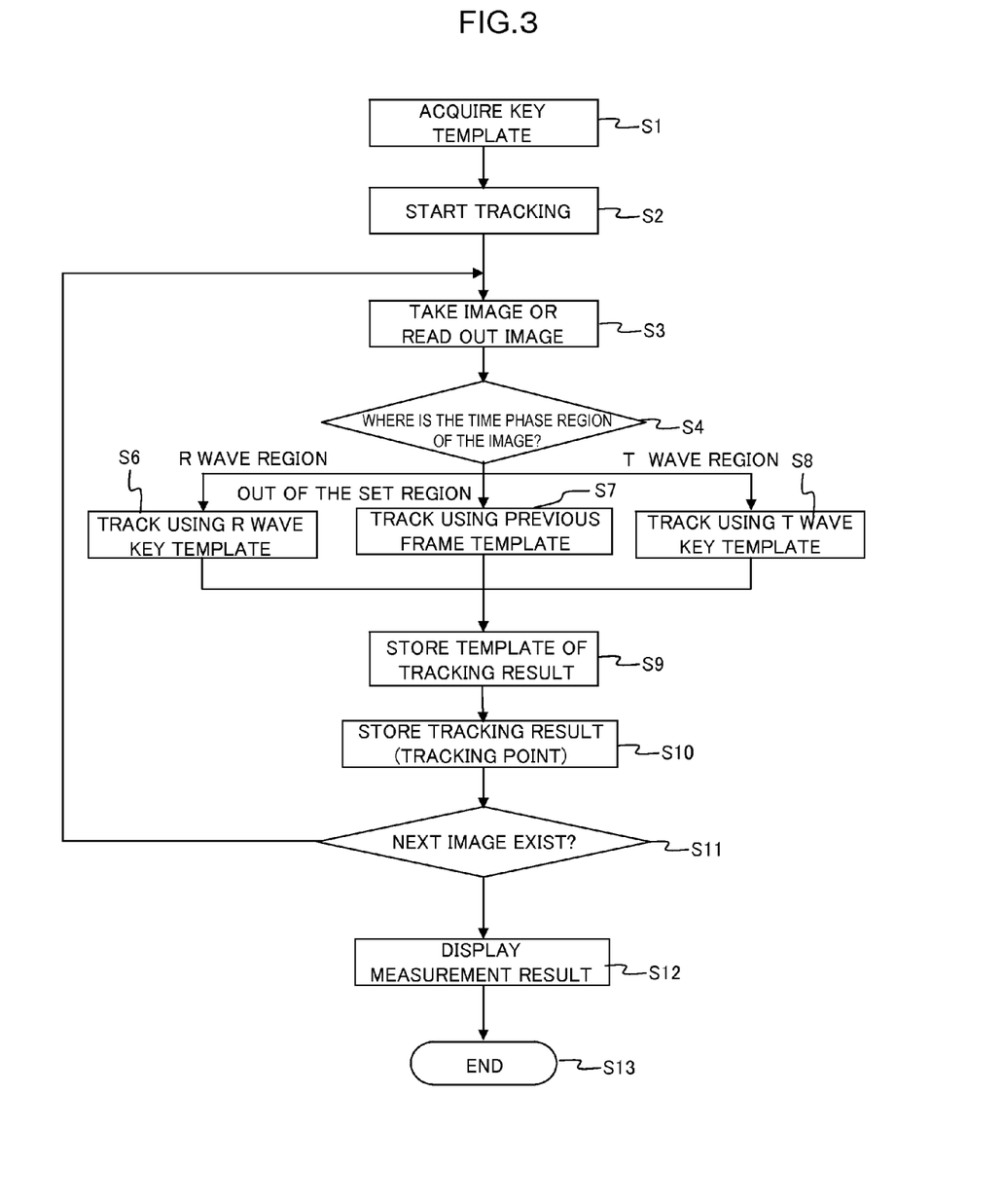
FIG. 3 is a flowchart for executing the tracking operation shown in FIG. 2.

Next, a first embodiment of the ultrasonic diagnostic apparatus of the invention will be described below. This embodiment is such that the tracking operation is performed while switching one or more key templates of cardiac phases according to the cardiac phases. With reference to FIGS. 2 and 3, this embodiment will be described specifically taking the tracking operation process for the tracking points set at one or a plurality of points on the image of the heart, a region of interest, of the test object that is displayed on the display screen of the display unit 12. This embodiment shows an example in which error correction for tracking points is performed at an R wave time phase and a T wave time phase during one cardiac cycle.

Before starting the tracking process, the examiner at first performs, as the preparation, an acquiring operation (S1) for key templates at a R wave cardiac time phase and a T wave cardiac time phase of the cardiac cycle. The acquiring operation for the key template is the same as described above, and therefore the description thereof will be omitted. It should be noted that the key template may be a template extracted by designating tracking points on an image at each of the P, Q, R, S, T, and U cardiac phases of an electrocardiographic waveform, in addition to the R wave and T wave, or the end-diastolic and end-systolic phases of the heart, a template extracted by the examiner designating positions of the tracking points on an image at an arbitrary cardiac phase with the input unit 3, or a template at a cardiac phase at the time when the tracking point setting unit 6 automatically sets tracking points. The key template at one or a plurality of cardiac phases acquired in this way is correlated with the time phase of the image from which the key template has been extracted and is stored in the template storing unit 7.

It should be noted the key templates stored in the template storing unit 7 are the templates of the actual tracking positions. Accordingly, when the key template is acquired at a greater number of time phases, the chances in which the tracking error is reduced are greater, and therefore, the advantageous effect of reducing the tracking error is obtained.

When the acquisition of the key template ends, the examiner manipulates the manipulator on the operation panel of the ultrasonic diagnostic apparatus or the tracking point tracking start switch displayed on the display screen of the display unit 12 to input a tracking point tracking start command (S2). The control unit 4, which has received the tracking start command signal, confirms that images for a period more than one cardiac cycle are stored in the image data storing unit 5, and reads out images for one cardiac cycle period from an R wave to the next R wave one after another from the image data storing unit 5 (S3). Since each of the image data stored in the image data storing unit 5 is provided with information indicating that the data corresponds to which time phase of the cardiac cycle, the control unit 4 determines to which time phase region the read-out image belongs, and which key template stored in the template storing unit 7 should be used to perform the template matching computation (S4). Then, the control unit 4 allows the template matching computation unit 8 to read out the corresponding template from the template storing unit 7 based on the determination results and to execute a template matching computation (S6, S7, and S8). Specifically, when it is determined that the read-out image belongs to the time phase of the R wave region, it instructs the template matching computation unit to execute the matching computation using an R wave key template (S6). When it is determined that the read-out image belongs to the time phase of the T wave region, it instructs the template matching computation unit to execute the matching computation using a T wave key template (S8). When it is determined that the read-out image falls outside the set region, it instructs the template matching computation unit to execute the matching computation using the template of the previous frame (image) (S7). In all the cases, the new template obtained from the image resulting from the template matching computation is correlated with the time phase of that image and stored in association in the template storing unit 7. It should be noted that the images offered for tracking the tracking points may not be the images stored in the image data storing unit 2 in advance, but they may be images taken by the ultrasonic probe 1 contacting with the test object and stored in sequence in real time (S3).

FIG. 2 shows which key template should be selected and used as the cardiac phase proceeds, and FIG. 2(*a*) is a view illustrating the concept of switching key templates according to the cardiac phase. Specifically, in the example shown in FIG. 2(*a*), during one cardiac cycle period between an R wave to an R wave in comparison with the electrocardiographic waveform, the template matching computation unit 8 performs the tracking operation by applying the key template of the R wave time phase in the vicinity of the R wave time phase (S6), while it performs the tracking operation by applying the key template of the T wave time phase near the T wave time phase (S8). Also, the template matching computation unit 8 performs the tracking operation by applying the template of the previous image, at the time phase of the period in which the key templates of the R wave time phase and the T wave time phase are not used (S7). In particular, at S7, the template of the next image is extracted in the next image to the last image in the R wave time phase region by the template matching computation using the R wave time phase key template, and this template is used for the template matching computation in the further next image. Subsequently, until reaching the T wave time phase region, a new template is extracted in each of the images to which the template matching computation is applied, using the template extracted in the previous image. Here, it is necessary to determine the number of frames that use the key template of the R wave time phase and the number of frames that use the key template of the T wave time phase. It is believed that they should be determined taking into consideration the frame rate of the ultrasonic wave imaging and the motion speed of the heart. For example, assuming that the frame rate of ultrasonic wave imaging is 30 frames/sec., appropriate frame numbers are about 2 to 5 frames at time phases near the R wave, about 2 to 5 frames in a preceding portion to the T wave, and about 5 to 10 frames at a succeeding portion to the T wave. However, there are variations in the cardiac cycle and pulsation among individuals, so it is possible that they can be set variably in the template extracting unit 9 as needed.

Hereinbelow, the template matching technique shown in FIG. 2(*a*) is described. First, the image of the first R wave time phase (first frame) is read out. Since the image of the R wave time phase is an image in which the examiner has set tracking points and a key template has been extracted, the control unit 4 outputs a command to the template matching computation unit 8 and so forth to perform a template matching computation for the next image (second frame) immediately. In other words, the template matching computation is skipped and the tracking points set by the examiner, as they are, are used for the image of the R wave time phase. Then, the second frame is read out from the image data storing unit 5, and the template matching computation is performed for the second frame using the key template of the R wave time phase, as described above.

Specifically, the small region having the greatest correlation value with the key template of the R wave time phase is extracted from the second frame as a template, and a tracking point is tracked (S6). The tracking point may be the center point in the extracted template. This small region extracted on the second frame is correlated with the time phase of the second frame and is stored in the template storing unit 7 as a template (S9). For the frames of the cardiac phase that exceed several frames of the time phase for which the tracking is performed using the key template of the R wave time phase, the template extracted in the respective previous frame is used to extract the small region having the greatest correlation value with that template and to track the tracking points (S7). The extracted small regions are stored in the template storing unit 7 as templates (S9). Then, as the cardiac phase proceeds further and the frame at which the template matching is performed using the key template of the T wave time phase is reached, the key template of the T wave time phase is read out from the template storing unit 7, and the template matching computation is performed. Subsequently, when the T wave time phase is reached, the template matching is not performed since the image of the T wave time phase is the image in which the examiner has set the tracking points and the key template is extracted, and the template matching computation for the next frame may be performed immediately.

In other words, the template matching computation is skipped and the tracking points set by the examiner, as they are, are used for the image of the T wave time phase, as in the case of the image of the R wave time phase. At this time, the template matching computation is performed for the next frame to the T wave time phase using the key template of the T wave time phase in a similar manner to that described above because it is close to the time phase of the T wave (S8). Then, when the time phase advances several frames and approaches the next R wave time phase, the cardiac phase falls in the time phase region for which the template matching is set to be performed using the template of the previous frame, so the template extracted in the previous frame is used to extract the small region having the greatest correlation value with that template as a template from the current frame and to track the tracking points (S7). Then, the extracted small region is correlated with the time phase of the current frame, and is stored in the template storing unit 7 as a template (S9). When the cardiac phase advances further and approaches the R wave time phase, the template matching computation is performed using the key template of the R wave time phase (S8). The small region having the greatest correlation value with the key template is extracted as a template from the current frame, and it is correlated with the time phase of the current frame and is stored in the template storing unit 7 (S9). Then, when the frame of the R wave time phase that is one cardiac cycle later than the first R wave is reached, the template matching computation is performed using the key template of the R wave time phase. It should be noted that the tracking points may be set automatically to the coordinates of the tracking points that have been set in the first frame without performing the template matching computation because the frame of the R wave time phase that is one cardiac cycle later than the first R wave normally yields the same image as that at the first frame. The same applies to the frame of the T wave that is one cardiac cycle later.

When the tracking operation for the first cardiac cycle ends as described above, the tracking operation is executed subsequently for the second cardiac cycle, the third cardiac cycle, the fourth cardiac cycle, ..., and the N-th cardiac cycle. The key template of the R wave time phase and the key template of the T wave time phase that have been used in the first cardiac cycle are used also for the second and later cardiac cycles. The tracking results (tracking points) obtained by the just-described tracking operation are correlated with the time phases of the images at which the tracking operation has been performed, and recorded in the measurement result recording unit 11 (S10). When the image data read out from the image data storing unit 5 finish (S11), the measurement results are displayed on the display unit (S12), and the tracking flow is completed (S13).

The process flow of FIG. 2(a) may be modified in various ways, and one example is shown in FIG. 2(b). In this example, only the template of the R wave time phase is employed as the key template. Specifically, in this example, the key template of the R wave time phase is applied when performing the template matching computation for the R wave time phase and several frames therebefore and thereafter, and the template extracted in the previous frame is used to the template matching computation for the other cardiac phase frames. By implementing this example as well, it is possible to track the pulsation of the heart by the error correction in the vicinity of the R wave time phase continuously and more accurately in comparison with the conventional techniques.

As has been described above, this embodiment can lessen accumulation of tracking errors by performing template matching using a key template at a predetermined time phase of the motion cycle over a lapse of time of motion of a moving organ. As a result, it becomes possible to maintain accuracy of tracking over a multiplicity of cycles of motion periods. Accordingly, it becomes possible to improve accuracy of various measurement values based on the tracking results.

SECOND EMBODIMENT

Figure 4:
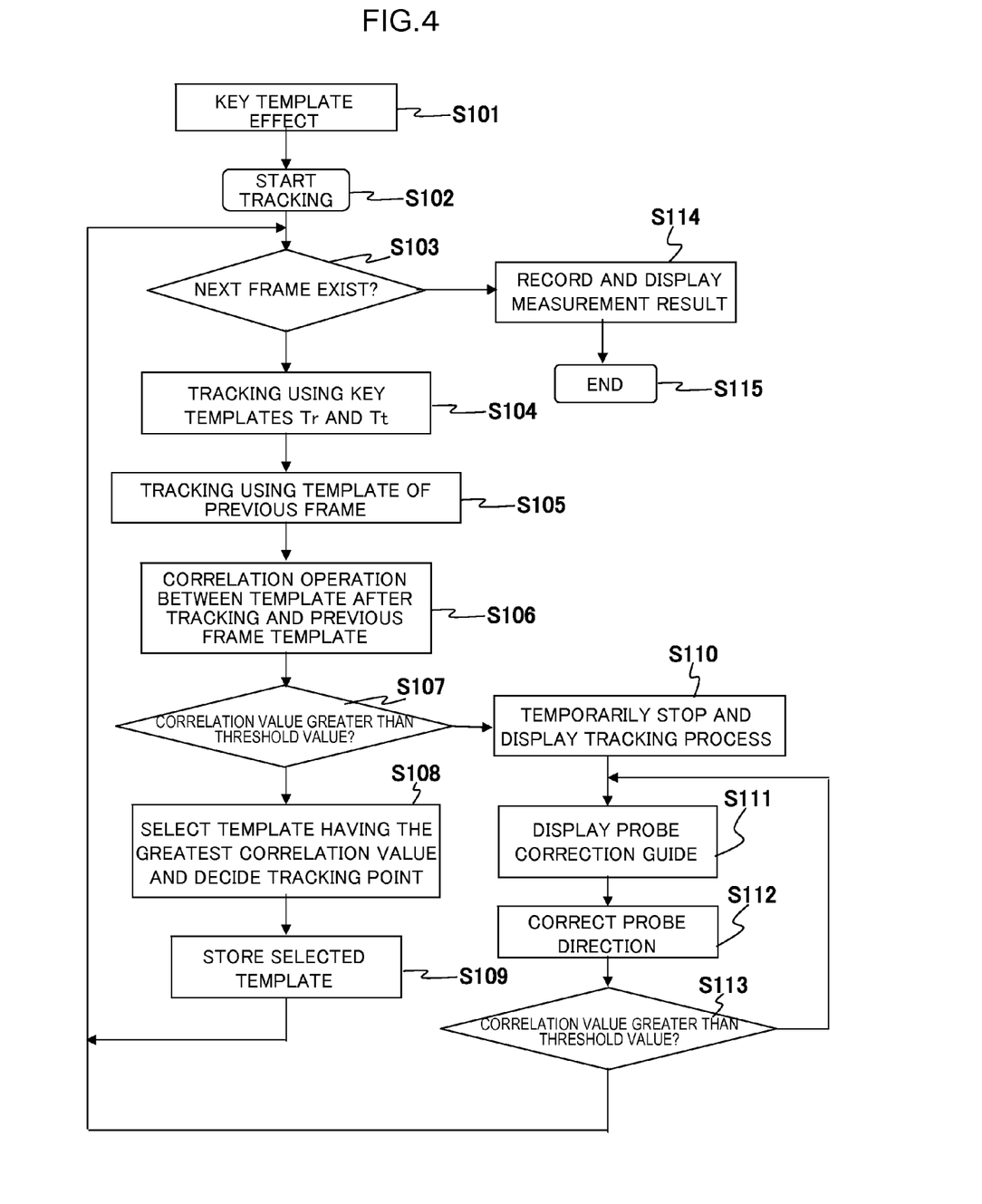
FIG. 4 is a flowchart for executing a tracking operation in a second embodiment of the invention.
Figure 5:
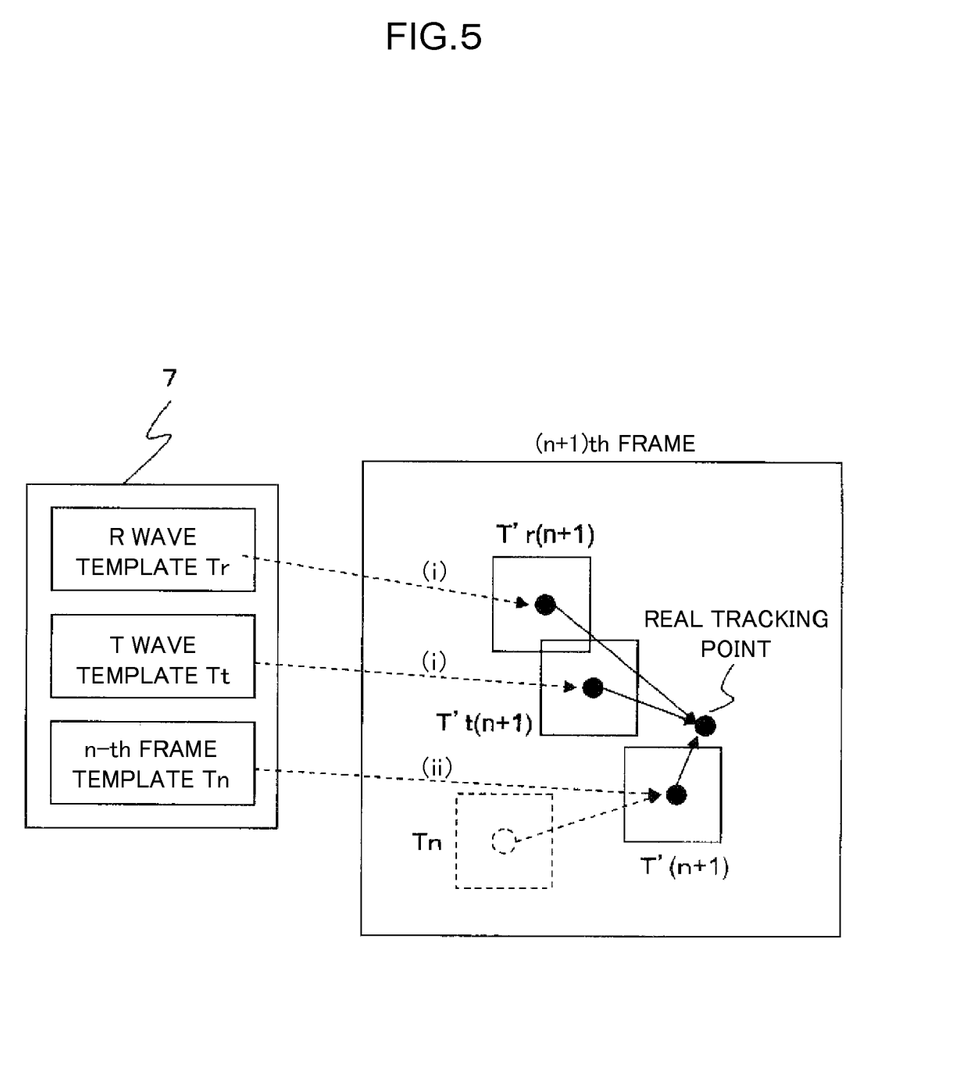
FIG. 5 is a flowchart for illustrating template matching in the second embodiment of the invention.

Next, a second embodiment of the invention will be described. The first embodiment above is such that a tracking operation is performed while switching one or more key templates of cardiac phases according to the cardiac phases. The second embodiment is such that the template matching is performed for an arbitrary frame (image) of a cardiac phase while using a plurality of key templates. Hereinbelow, this embodiment will be described with reference to FIGS. 4 and 5. The template matching starts with the step of acquiring key templates for the R wave cardiac phase and the T wave cardiac phase, correlating the key templates with the respective time phases, and storing them in the template storing unit 7 (S101), as in the process flow shown in FIG. 3. When the acquisition of the key templates ends, the control unit 4 starts a tracking process (S102). If the next frame for which an ultrasonic image of the heart is read out from the image data storing unit 5 exists (S103), the process is performed as follows. FIG. 5 shows a case in which tracking is performed for a tracking point at the position in a template Tn of an arbitrary read-out frame (the n-th frame) to that of the next frame (the (n+1)th frame).

This computation will be described in detail. The position of the template Tn shown in FIG. 5 is the position of the tracking point obtained by the tracking operation for the arbitrary frame (the n-th frame) after starting the tracking. First, the template matching computation unit 8 reads out the R wave time phase key template Tr and the T wave time phase key template Tt, which are stored in the template storing unit 7 for the (n+1)th frame, and performs tracking processes using the key templates in the (n+1)th frame (S104). This tracking process is a process for finding the small region that is most similar to the key template Tr or the key template Tt in the vicinity of the position of the template Tn of the n-th frame within the image of the (n+1)th frame. The position of the most similar small region becomes the tracking result (tracking point). For this small region containing the tracking point, a small region T'r(n+1) of the (n+1)th frame, and a small region T't(n+1) of the (n+1)th frame are obtained as the result of tracking using the R wave time phase key template Tr and the result of tracking using the T wave time phase key template Tt, respectively. (The process (i) in FIG. 5).

Next, the template matching computation unit 8 performs a tracking process using the template Tn of the n-th frame (the previous frame) (S105). That is, it performs a process for finding the small region that is most similar to the template Tn in the vicinity of the position of the template Tn of the n-th frame within the (n+1)th frame. The position of the most similar small region becomes the tracking result (tracking point). This small region containing the tracking point is obtained as a small region T'(n+1) of the (n+1)th frame, as the result of tracking using the template Tn of the n-th frame. (The process (ii) in FIG. 5).

Next, the template extracting unit 9 calculates a correlation value between Tn and T'r(n+1), a correlation value between Tn and T't(n+1), and a correlation value between Tn and T'(n+1) (S106). It is evaluated that whether each of these correlation values is higher or lower than a predetermined threshold value (S107). If there exists a correlation value higher than the threshold value, the template having the greatest correlation value with the template Tn of the n-th frame is adopted to decide the tracking point (S108). In other words, the tracking point in the adopted template is adopted as the tracking result. Here, a known correlation method, such as a common cross-correlation function, a sum of absolute differences, and a sum of squared differences, may be used for the calculation of the correlation values. Then, the template selected for deciding the tracking point is correlated with the time phase of the next frame and is stored in the template storing unit 7 as a template T (n+1) for the tracking operation for the next frame (S109).

The process flow described above is performed repeatedly for the frames (images) that are read out one after another. When the process for the last image ends, the measurement result of the tracking point is recorded in the measurement result recording unit 11 and is displayed on the display unit 12 together with the image (S114), and the process flow ends (S115).

When the correlation value exceeds a predetermined threshold value and the correlation value between Tn and T'r(n+1) is the greatest, the time phase of the (n+1)th frame is close to the time phase of the R wave, so the operation is performed in such a manner that the tracking point approaches the (assumed) real tracking position in the R wave to eliminate cumulative errors. Likewise, when the correlation value between Tn and T't(n+1) is the greatest, the time phase of the (n+1)th frame is close to the time phase of the T wave, so the operation is performed in such a manner that the tracking point approaches the (assumed) real tracking position in the T wave to eliminate cumulative errors. When the correlation value between Tn and T'n(n+1) is the greatest, the time phase of the (n+1)th frame is close to neither the time phase of the R wave nor that of the T wave, so the tracking operation is performed using the template Tn of the n-th frame.

When seeing the correlations in the time phases of the R wave and the T wave in this embodiment, it follows that the correlation containing the key template of the R wave time phase shows the greatest value for the correlation value in the R wave, while the correlation containing the key template of the T wave time phase shows the greatest value for the correlation value in the T wave.

The second embodiment of the invention has described an example in which template matching is performed at an arbitrary time phase using the key template of the R wave time phase and the key template of the T wave time phase. However, it is possible to consider that, for example, the tracking point in the R wave of the next cardiac cycle return at the same position as that in the R wave of the current cardiac cycle because of the periodicity of the heart. Therefore, in the R wave time phase, the tracking may be performed using only the key template of the R wave time phase, while in other time phases, the tracking may be performed using the key template of the R wave time phase and the key template of the T wave time phase. In addition, the foregoing description has shown an example in which tracking using the previous frame template (S105) is performed subsequent to the tracking using a key template (S104). However, this sequence may be the other way round. Alternatively, only the tracking using one of them may be performed and the other one may be omitted according to the cardiac cycle time phase.

The tracking point tracking operation of the invention described thus far is a process in a forward time order at all times, in other words, a process that does not require correction of past data by current data. Therefore, it is suitable as a technique for tracking a tracking point in real time.

As described above, in this embodiment, template matching is performed for a frame (image) of an arbitrary cardiac phase using a plurality of key templates. Therefore, accumulation of tracking errors can be further lessened in comparison with the advantageous effects of the first embodiment. As a result, it becomes possible to further improve the accuracy of various measurement values based on the tracking results by further improving the tracking accuracy over a multiplicity of cycles of motion periods.

(Correction Assistance for Ultrasonic Probe Holding Direction Etc.)

Next, the following describes correction assistance for ultrasonic probe holding directions and the like, which is applicable commonly to the first embodiment and the second embodiment, in the case that tracking becomes difficult. In the following, the present correction assistance will be described taking an example in which it is applied to the second embodiment above, with reference to FIGS. 4 and 6.

Figure 6:
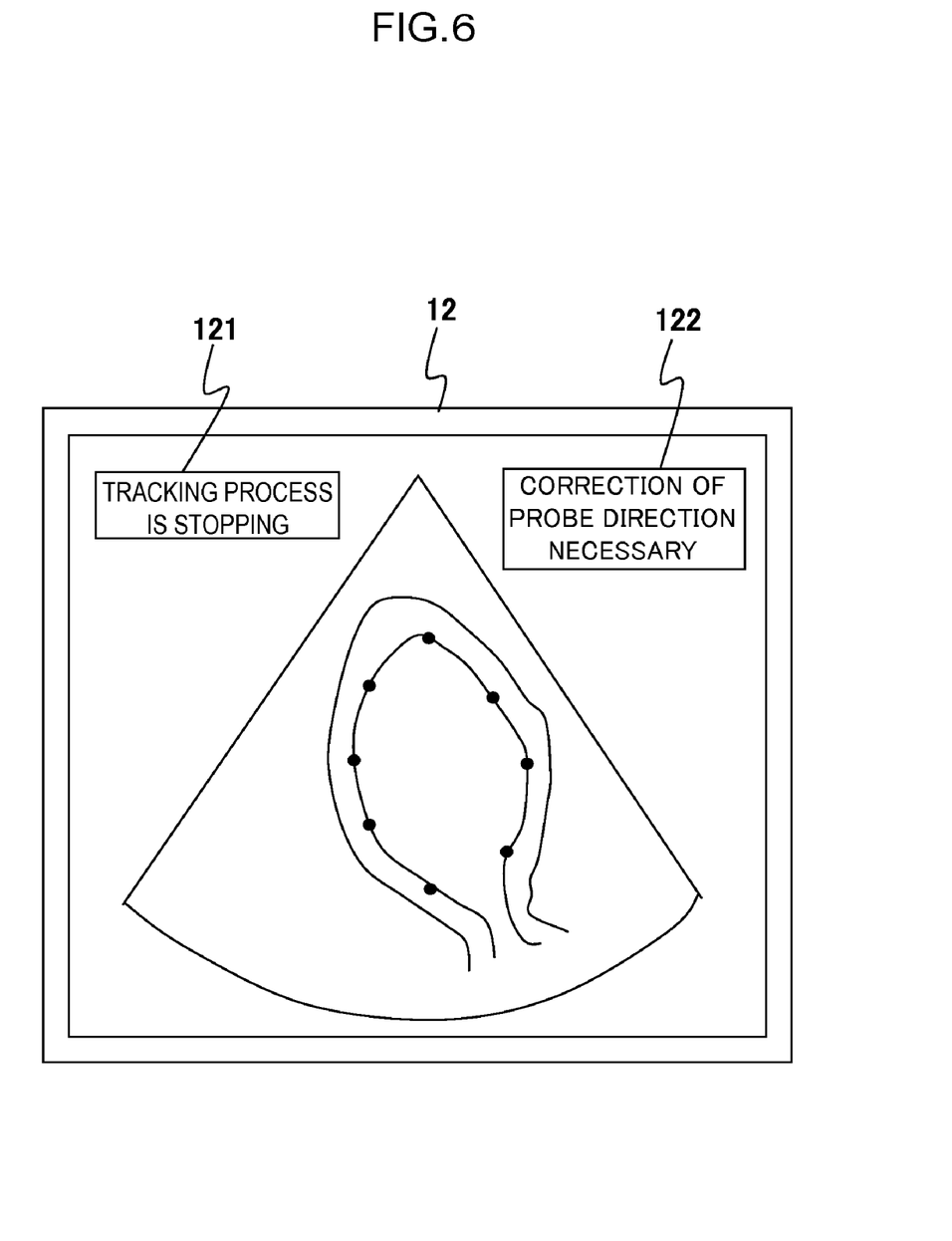
FIG. 6 is a view showing a display screen of a display unit when template matching becomes inexecutable.

It is believed that the error in the template matching itself is large when all the correlation values are determined as being equal to or less than the predetermined threshold value at S107. At this time, it is determined that there was a misoperation such that the examiner shifted the direction of the probe, so the control unit 4 automatically stops the tracking process and allows the display screen of the display unit 12 to display information or a comment 121 indicating that the tracking process is being stopped (S110). Subsequent to S110, the control unit 4 allows the display screen of the display unit 12 to display guide information 122 indicating that the examiner needs to correct the holding direction of the probe (S111). At this time, an actual ultrasonic image showing the direction in which the examiner points the probe is displayed continuously on the display screen, as shown in FIG. 6, and the tracking points (dots in FIG. 6) are superimposed thereon. These tracking points are displayed in moving image so that the current cardiac cycle is in accordance with one cardiac cycle during the normal period before the tracking was stopped. By referring to this, the examiner recognizes that the tracking points do not match the image, i.e., the direction of the probe has shifted, so the examiner adjusts the direction of the probe so that an image with approximately the same positions as those before the tracking was stopped (S112). When the key template is set to be the R wave time phase template in the image after adjusting the direction of the probe, for example, a correlation value is obtained between the R wave time phase key template and a template in which a superimposed tracking point and an adjacent small region thereto are taken out, and if the value exceeds a predetermined threshold value, the tracking is restarted automatically (S113). Alternatively, it is possible to adjust the direction of the probe using the information for only the R wave time phase by, not displaying a moving image for one cardiac cycle, but displaying the tracking points at the R wave time phase before stopping the tracking, which were properly tracked, at S112 and displaying only the image for the R wave time phase in real time intermittently.

The tracking operation process is performed until either the examiner performs a tracking stop operation, for example, by giving an instruction by operating a freeze button on the input unit 3, or there is no more next frame to be tracked.

In the case of actual test, it is difficult to keep taking the images at the same position by placing the probe at the same position for a long time because there are movements of the patient. According to the correction assistance of the invention, the examiner only needs to operate the probe from the stopping of the tracking process to displaying of the correction guide and restarting of the tracking process. Thus, it is possible to carry out a test that can reduce the burden on the examiner.

(Measurement Based on Tracking Process Result)

At the same time as performing the tracking process, the measurement computation unit 10 calculates measurement values such as displacement of the tissue, speed, cardiac muscle wall thickness, area, heart chamber volume and the like in the case of heart, based on the tracking process results over a period of one cardiac cycle or longer. The measurement values are recorded by the measurement result recording unit 11 immediately after the calculation, and displayed on the display unit 12. These may be superimposed in a table or a graph on the B mode image on the display screen.

Figure 8:
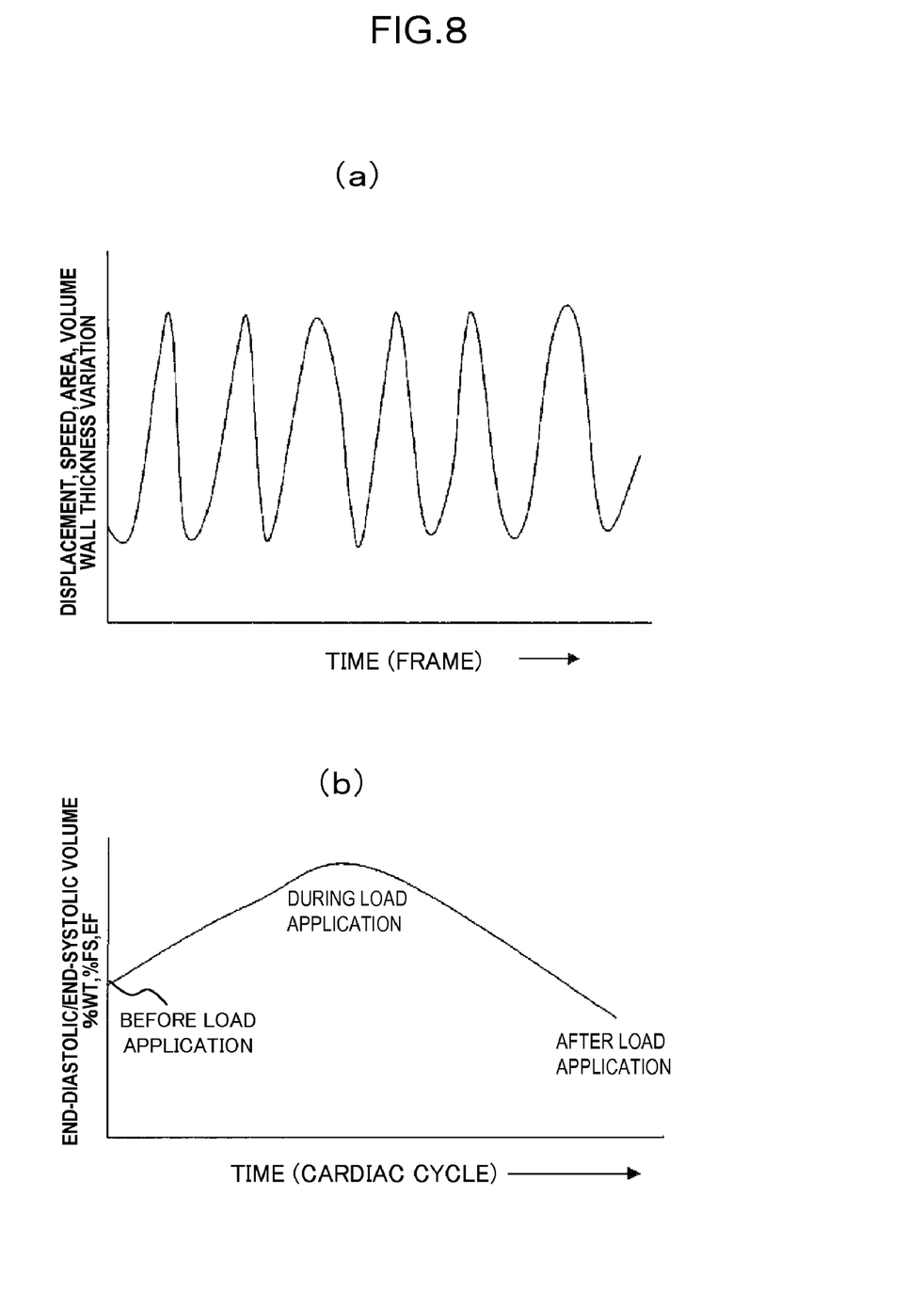
FIG. 8 shows views illustrating how physical parameters measured using tracking points measured and computed by a measurement computation unit are displayed.

These values may be displayed in real time as shown in FIG. 8(a), taking displacement, speed, area, volume, wall thickness variation of the portion of interest along the vertical axis, and taking time or frame along the horizontal axis. In a test in which a load is applied to the heart and cardiac functions are observed before and after the load application, end-systolic volume and end-diastolic volume may be taken as the measurement values along the vertical axis while time or cardiac cycle may be taken along the horizontal axis, as shown in FIG. 8(b). In this way, the systolic function and the diastolic function of the heart can be observed and evaluated in real time, which is useful for diagnosis of ischemic heart diseases. Ejection fraction (EF) and left ventricle fractional shortening (% FS) are also useful for the diagnosis. In addition, regional wall motion evaluation can be performed by measuring the rate of change of cardiac muscle wall thickness (% WT: wall thickening).

According to the measurements based on the tracking process results of the invention, the accuracy of the tracking operation can be maintained over a period of one cardiac cycle or longer. Therefore, it becomes possible to acquire various measurement values with high accuracy over a period of one cardiac cycle or longer.

The invention claimed is:

1. A medical diagnostic imaging apparatus, comprising:
   an image data acquiring unit for acquiring a plurality of images of a moving organ of a test object that moves periodically;
   a display unit for displaying the images acquired by the image data acquiring unit;
   a matching computation unit for performing a matching computation between a template extracted containing a tracking point on one image and another image;
   a template extracting unit for extracting, from the other image, a region correlated with the template as a template of the other image by the matching computation;
   a storing unit for correlating the template with a time phase at which it has been extracted and storing the template therein; and
   a control unit for controlling each of the units,
   the medical diagnostic imaging apparatus being for tracking a movement of the tracking point based on the extracted template,
   wherein the template extracting unit extracts, as a key template, a region containing one or more tracking points set on an image at least one selected time phase of the moving organ, and
   wherein the matching computation unit performs the matching computation using the key template in the vicinity of the time phase at which the key template is extracted.

2. The medical diagnostic imaging apparatus as set forth in claim 1,
   wherein the storing unit correlates a key template extracted at least one time phase of the moving organ with a respective time phase and stores therein, and
   wherein the matching computation unit reads out a key template corresponding to the time phase of an image to be subjected to the matching computation from the storing unit, and performs the matching computation for the image using the read-out key template.

3. The medical diagnostic imaging apparatus as set forth in claim 2,
   wherein at a plurality of time phases of the moving organ, the template extracting unit extracts, as key templates, regions each containing a tracking point set on an image of each of the time phase, and
   wherein the matching computation unit performs the matching computation using the respective key templates in the vicinities of the plurality of time phases at which the key templates are extracted.

4. The medical diagnostic imaging apparatus as set forth in claim 3,
   wherein the template extracting unit extracts at least one key template of a key template of an R wave time phase from an image of the R wave time phase and a key template of a T wave time phase from an image of the T wave time phase.

5. The medical diagnostic imaging apparatus as set forth in claim 3,
   wherein the template extracting unit extracts at least one key template of a key template of an end-diastolic phase from an image of the end-diastolic phase and a key template of an end-systolic phase from an image of the end-systolic phase.

6. The medical diagnostic imaging apparatus as set forth in claim 3,
   wherein the display unit displays guide information for urging that the same number of key templates is correlated with each other and extracted in a plurality of images with different time phases.

7. The medical diagnostic imaging apparatus as set forth in claim 1,
   wherein the template extracting unit extracts, as the key template, a small region of 40 pixels×40 pixels containing the set tracking point.

8. The medical diagnostic imaging apparatus as set forth in claim 1,
   wherein the matching computation unit performs the matching computation using the key template in images of 2 through 5 frames before and after the time phase at which the key template is extracted.

9. The medical diagnostic imaging apparatus as set forth in claim 1,
   wherein the matching computation unit performs the matching computation using the key template in the vicinity of the time phase at which the key template is extracted, repeatedly over a plurality of motion cycles.

10. The medical diagnostic imaging apparatus as set forth in claim 1, wherein the matching computation unit skips the matching computation in the image at the time phase at which the key template is extracted.

11. The medical diagnostic imaging apparatus as set forth in claim 1,
wherein the template extracting unit extracts, from an image that has been subjected to the matching computation using the key template, a region correlated with the key template as a template of the image, and
wherein the matching computation unit performs the matching computation using the template in a next image to the image from which the template is extracted.

12. The medical diagnostic imaging apparatus as set forth in claim 11,
wherein the matching computation unit performs the matching computation in the next image using the template extracted in a previous image, in other time phases than the vicinity of the time phase at which the key template is extracted.

13. The medical diagnostic imaging apparatus as set forth in claim 1,
wherein the control unit stops the matching computation by the matching computation unit to stop tracking of movement of the tracking point and allows the display unit to display information indicating that the matching computation is being stopped, if a correlation value based on the matching computation is equal to or less than a predetermined threshold value.

14. The medical diagnostic imaging apparatus as set forth in claim 13,
wherein the control unit reads out a key template or a template corresponding to a time phase of an actual ultrasonic image displayed on the display unit from the storing unit, and allows the display unit to superimpose the key template or a tracking point contained in the template on the actual ultrasonic image in accordance with the time phase thereof.

15. The medical diagnostic imaging apparatus as set forth in claim 14,
wherein the template extracting unit extracts a template containing the tracking point superimposed on the actual ultrasonic image,
wherein the matching computation unit performs a matching computation between the template extracted containing the tracking point superimposed on the actual ultrasonic image and the key template in the vicinity of the time phase at which the key template is extracted,
wherein the control unit restarts tracking of movement of the tracking point that has been stopped, if a correlation value based on the matching computation exceeds a predetermined threshold value.

16. The medical diagnostic imaging apparatus as set forth in claim 13,
wherein the display unit displays guide information indicating that it is necessary to correct a way of acquiring the image.

17. The medical diagnostic imaging apparatus as set forth in claim 1,
wherein the matching computation unit performs a matching computation in a next image using a plurality of different time phases in the key template or the template,
wherein the template extracting unit extracts, as a template of the next image, a region of the next image having the greatest correlation value based on the matching computation.

18. The medical diagnostic imaging apparatus as set forth in claim 1, further comprising:
an ultrasonic probe for performing ultrasonic wave transmission and reception to and from the moving organ,
wherein the image data acquiring unit acquires a plurality of images of the moving organ based on a reception signal from the ultrasonic probe.

19. A tracking point tracking method of tracking a desired tracking point over a plurality of images of a moving organ of a test object that moves periodically by a matching computation using a template, comprising the steps of:
(a) setting the tracking point on one image;
(b) extracting a region containing the tracking point as a template;
(c) extracting, by a matching computation between the template and another image, a region correlated with the template from the other image as a new template; and
(d) repeating the template extracting step (c) while changing the images,
wherein in the step (a), one or more tracking points are set on an image of a desired time phase of the moving organ,
wherein in the step (b), a region containing one or more tracking points set on the image of the desired time phase is extracted as a key template, and
wherein in the step (c), the matching computation is performed using the key template in the vicinity of the time phase of the image in which the key template is extracted.

20. The tracking point tracking method as set forth in claim 19,
wherein the step (c) comprises the steps of:
(e) extracting, using the key template, a region correlated with the key template on the other image as a template;
(f) extracting, using the template, a region correlated with the template on a next image to the other image as a template of the next image;
(g) repeating the template extracting step (f) while changing the images; and
(h) performing, using the key template, the matching computation for an image in the vicinity of the time phase at which the key template is extracted.

* * * * *